United States Patent

Balzer

Patent Number: 5,858,954
Date of Patent: Jan. 12, 1999

[54] MICROEMULSION CLEANING COMPOSITIONS CONTAINING SURFACTANT

[75] Inventor: Dieter Balzer, Haltern, Germany

[73] Assignee: Huels Aktiengesellschaft, Marl, Germany

[21] Appl. No.: 839,788

[22] Filed: Apr. 16, 1997

[30] Foreign Application Priority Data

Apr. 18, 1996 [DE] Germany .................. 196 15 271.2

[51] Int. Cl.$^6$ .............................. C11D 1/825; C11D 3/44
[52] U.S. Cl. .................. 510/417; 510/130; 510/159; 510/365; 510/422; 510/434; 510/470; 510/505
[58] Field of Search ................................ 510/417, 365, 510/434, 238, 470, 477, 130, 159, 422, 505

[56] References Cited

U.S. PATENT DOCUMENTS 5,196,136  3/1993  Dishart et al. ..................... 252/170
5,707,957  1/1998  Yianakipoulos et al. ............ 510/424

FOREIGN PATENT DOCUMENTS

0137616A1  4/1985  European Pat. Off. .
0160762A1  11/1985  European Pat. Off. .
WO92/03528  3/1992  WIPO .

OTHER PUBLICATIONS

Lüders, H., et al, Synthesis, Chemical Structures and Properties of Alkyl Polyglucosides, Hüls AG, Paul–Baumann–Str. 1, D–4370 Marl, pp. 81–93.

Langevin, D., Microemulsions and Liquid Crystals, Mol. Cryst. Liq. Cryst, 1986, vol. 138, pp. 259–305.

Primary Examiner—Paul Lieberman
Assistant Examiner—Gregory E. Webb
Attorney, Agent, or Firm—Oblon, Spivak, McClelland, Maier & Neustadt, P.C.

[57] ABSTRACT

The invention relates to cleaning compositions in the form of microemulsions for cleansing the skin or for the manual cleaning of hard surfaces. These cleaning compositions consist of oil, water, surfactant and cosolvent. As surfactant, use is made of a surfactant system consisting of 80–100% alkylpolyglycoside and 0–20% auxiliary surfactant, of anionic, nonionic or betaine type, whose choice is largely arbitrary. The cosolvent is an oligoester of polybasic carboxylic or hydroxycarboxylic acids with $C_1$ to $C_4$ alcohols. The microemulsions are highly stable and can be diluted in water without problems.

20 Claims, No Drawings

MICROEMULSION CLEANING COMPOSITIONS CONTAINING SURFACTANT

BACKGROUND OF THE INVENTION

1. Field of the Invention

The invention relates to mild, surfactant-containing compositions in the form of microemulsions for cleansing the skin and for cleaning hard surfaces.

2. Description of the Related Art

While the use of macroemulsions as cleaning compositions for virtually all surfaces has long been known, corresponding microemulsions have been described only recently. In contrast to thermodynamically metastable macroemulsions, microemulsions are equilibrium systems, and are therefore completely stable. Based on the high level of fine division of the system, its free energy is negative as a result of the strong increase in dispersion entropy, despite the infinite, although very small, surface tension, and the system is therefore stable. A consequence of the fine division—diameters of around 10 nm (5 to 100 nm) are typical as opposed to >1 $\mu$m in the case of macroemulsions—is the transparency or translucency of the liquids. Microemulsions therefore often give the impression of being true solutions. They consist of the two mutually immiscible liquids, generally water and an apolar liquid, of the surfactant or surfactant mixture, and usually of a cosolvent, occasionally also referred to as cosurfactant. Typical cosolvents are lower alcohols of 3 to 5 carbon atoms. Their effect is firstly to reduce the surface tension between the two liquids, as well as that of the surfactant, and additionally to model the interfacial film (cf. D. Langevin, Mol. Cryst. Liquid Cryst. 1986, 138, 259–305).

Microemulsions as cleaning systems have been described since the mid-1980s. For instance, the patent applications EP-A-0 137 616 and EP-A-0 160 762 claim liquid heavy-duty detergents in the form of an O/W microemulsion consisting of terpenes, paraffins, alkyl-aromatics and/or halogenated hydrocarbons as fat-dissolving solvents, water, customary surfactants, especially based on petrochemicals; electrolytes and amines as stabilizers. Cleaners for hard surfaces that are in the form of microemulsions are claimed by EP-A-0 316 726, EP-A-0 368 146, EP-A-0 620 271 and DE-A-37 16 526. They comprise customary surfactants, cosolvents such as water-soluble alcohols, polypropylene glycols, monoalkyl ethers of glycols, aliphatic carboxylic acids or phosphoric esters, in addition to fragrances and/or hydrocarbons as apolar liquids and, if desired, electrolyte. Finally, the documents EP-A-0 478 086 and WO 92/03528 describe specific cleaners having disinfecting and abrasive properties, respectively, for hard surfaces, that are in the form of microemulsions. They are based on customary, predominantly petrochemical surfactants and customary cosolvents, the latter document making mention, alongside many other types of surfactant, of alkylpolyglucosides.

The use of alkylpolyglucosides as a basic surfactant in microemulsions has been known for some years (cf. H. Luders and D. Balzer, Proc. 2nd World Surfactant Congr. 1988, Paris, Vol. II, 81–93). Nevertheless, this property, unlike that of, for example, fatty alcohol oxethylates, was always associated with the use of customary cosolvents, such as $C_3$–$C_6$ alcohols, alkylglycols, alkyloligoglycols, amines, etc., all of which are unacceptable in odor and/or objectionable on toxicological grounds, so that there is virtually no question of using these microemulsion systems as manual cleaning liquids, let alone in cosmetic applications. In the context of the latter, however, alkylpolyglucosides are of particular interest. Thus, human toxicological tests (DKT) have shown that these compounds are particularly skin-friendly in comparison with other surfactants widely used in cosmetology. The reason for this may lie in the lower degreasing effect in comparison with, say, fatty alcohol ether sulfates, as has been shown in degreasing tests on pigskin loaded with radiolabeled sebum.

This greater skin mildness is also achieved in the case of mixtures of $C_{10}C_{12}$-and/or $C_{12}C_{14}$-alkylpolyglucosides with ether sulfates, as shown by the much higher residual radioactivity in relation to pure ether sulfate. Consequently, it should also be possible to use alkylpolyglycosides in the form of aqueous microemulsions for cosmetic applications in particular. Similar comments apply to all cleansing processes where the surface of the skin may come into contact with the cleansing liquid. Implicit in this objective, however, is that it is possible to find suitable cosolvents which do not have the above-mentioned disadvantages but are toxicologically unobjectionable and at least neutral in terms of odor.

SUMMARY OF THE INVENTION

The present invention, which overcomes the problems noted above, is achieved by the novel combination of surfactant and cosolvent. Accordingly it is possible, surprisingly, to prepare microemulsions having high oil and water contents by means of alkylpolyglycosides, alone or in combination with small amounts of other surfactants, and esters of polybasic carboxylic or hydroxycarboxylic acids with $C_1$–$C_4$ alcohols as cosolvents.

The invention therefore provides a cleaning composition for cleansing the skin or for the manual cleaning of hard surfaces, in the form of a microemulsion consisting essentially of oil, water, surfactant and cosolvent, wherein the surfactant system comprises 80–100% alkylpolyglycosides and 0–20% auxiliary surfactants, and the cosolvent consists of oligoesters of polybasic carboxylic or hydroxycarboxylic acids with alcohols of 1 to 4 carbon atoms, and mixtures thereof.

The invention additionally provides for the use of the cleaning composition for cleansing the skin and for the manual cleaning of hard surfaces.

The novel microemulsions contain 0.3 to 50% oil phase, 1 to 60% surfactant, 0.5 to 50% cosolvent and 15 to 97% water. Preference is given to an oil content of from 0.5 to 45%, a surfactant content of from 3 to 55%, a cosolvent content of from 1 to 45% and a water content of from 18 to 95%. Particular preference is given to contents of 1 to 40% of oil, 5 to 50% of surfactant, of 3 to 40% of cosolvent and of 20 to 93% of water.

DETAILED DESCRIPTION OF THE PREFERRED EMBODIMENTS

Oils

Particularly suitable oil phases are the oils employed in cosmetology, for example natural and synthetic triglycerides of various fatty acids and also their di- and monoglycerides, fatty acid esters of lower alcohols, such as isopropyl fatty acid esters, liquid paraffins, castor oil, and also mixtures thereof, with or without additions of up to 20% of fatty alcohols, terpenes and other odoriferous substances, and also silicone oils and mixtures thereof.

Surfactants

The alkylpolyglycosides employed in accordance with the invention are of the formula (I)

$$R\text{—}O\text{—}Z_n \tag{I},$$

in which R is a linear or branched, saturated or unsaturated aliphatic alkyl radical of 8 to 16 carbon atoms, or mixtures thereof, and $Z_n$ is a polyglycosyl radical where n=1 to 3 hexose or pentose units or mixtures thereof.

Preference is given to alkylpolyglycosides containing a polyglycosyl radical where n=1.1 to 2 glycosyl units, very preferably where n=1.1 to 1.6 glycosyl units. Preferred alkylpolyglycosides are alkylpolyglucosides.

The alkylpolyglycosides can be prepared by known methods on the basis of renewable raw materials. For example, dextrose is reacted in the presence of an acidic catalyst with n-butanol to form butyl(poly)glucoside mixtures, which are transglycosidated with long-chain alcohols, likewise in the presence of an acidic catalyst, to form the desired alkylpolyglucoside mixtures. Alternatively, dextrose is reacted directly with the desired long-chain alcohol.

The structure of the products can be varied within certain limits. The alkyl radical R is determined by the selection of the long-chain alcohol. Favorable on economic grounds are the industrially obtainable surfactant alcohols with 8 to 16 carbon atoms, especially native fatty alcohols from the hydrogenation of fatty acids and/or fatty acid derivatives. It is also possible to use Ziegler alcohols or oxo alcohols.

The polyglycosyl radical $Z_n$ is determined firstly by the selection of the carbohydrate and secondly by the establishment of the mean degree of polymerization n, for example in accordance with DE-A-19 43 689. In principle it is possible to employ polysaccharides such as, for example, starch or maltodextrins and dextrose, etc. Preference is given to the use of dextrose, which is readily obtainable industrially. Since the economically advantageous alkylpolyglycoside syntheses do not proceed regio- and stereoselectively, alkylpolyglycosides are always mixtures of oligomers, which in turn constitute mixtures of different isomeric forms. n is a mean value, which therefore may also not be an integer. The alkylpolyglycosides are present alongside one another with α- and β-glycosidic linkages in pyranose form and furanose form. The linkage sites between two saccharide radicals are also variable.

Alkylpolyglycosides employed in accordance with the invention can also be prepared by blending alkylpolyglycosides with alkylmonoglycosides. The latter can be obtained or enriched, for example, in accordance with EP-A-0 092 355, by means of polar solvents, such as acetone, from alkylpolyglycosides.

The degree of glycosidation can expediently be determined by means of high-temperature gas chromatography of the silylated alkylpolyglycosides.

Ecologically, the alkylpolyglycosides are among the most environment-friendly surfactants. This in the course of testing the biodegradability (couplet unit test, DOC measurement), $C_{10}C_{12}$- and $C_{12}C_{14}$-alkylpolyglucosides were found to give values of 95 to 97%.

The toxicity data with LD 50 (rat >10,000 mg/kg LC 50 (golden orfe) 12–40 mg/l and EC 50 (Daphnia) 30–110 mg/l for in each case 2 $C_{10}C_{12}$- and $C_{12}C_{14}$-alkylpolyglucosides likewise point to an outstanding environmental behavior in comparison with many other surfactants, even customary silicone antifoam dispersants.

In some cases it may be expedient to combine the alkylpolyglycoside with up to 20%, preferably up to 15%, particularly preferably up to 10%, based on the overall amount of surfactant, of auxiliary surfactant. Suitable auxiliary surfactants are anionic surfactants such as $C_8$–$C_{18}$ fatty alcohol sulfates, $C_8$–$C_{18}$ fatty alcohol ether sulfates with 1 to 3 mol of ethylene oxide/mol, carboxymethylated $C_{10}$–$Cl_{18}$ fatty alcohol oxethylates with 3 to 10 mol of ethylene oxide/mol, ethoxylated $C_{10}$–$C_{18}$ fatty alcohol sulfosuccinates with 2 to 6 mol of ethylene oxide/mol, nonionic surfactants such as $C_{10}$–$C_{18}$ oxethylates with 3 to 50 mol of ethylene oxide/mol, $C_8$–$C_{14}$ fatty acid N-alkylglucamides, ethoxylated and nonethoxylated sorbitan esters of the Tween or Span type, and also betaine surfactants of the type of the alkylamidopropylbetaines, and mixtures thereof.

Cosolvents

Novel cosolvents are oligoesters of polybasic carboxylic acids and/or hydroxycarboxylic acids with lower alcohols ($C_1$–$C_4$). Preference is given to esters of polybasic $C_2$- to $C_6$-carboxylic or hydroxycarboxylic acids. Particular preference is given to the esters of the polybasic $C_2$- to $C_4$-carboxylic acids with $C_2$ to $C_4$ alcohols. Examples of typical cosolvents are diethyl tartrate, diisopropyl tartrate, di-n-propyl tartrate, dibutyl tartrates, triethyl citrate, etc.

Further Constituents

Further constituents of the microemulsion, in addition to water, may be electrolytes, colorants, clouding agents, preservatives, etc.

In general, the preparation of the novel aqueous microemulsions is unproblematic, since the systems involved are equilibrium systems, unlike macroemulsions. One method for their preparation consists, for example, in first of all combining the oil phase, cosolvent and surfactants with stirring and then diluting the mixture with water. The oil-water ratio should be from 1:1000 to 3:1, preferably from 1:500 to 2:1, while the surfactant-cosolvent ratio is from 1:3 to 100:1, preferably from 1:2 to 50:1.

The pH of the cleaning compositions is not insignificant, and should be in the neutral range from 5 to 8.

The present invention is illustrated more specifically by referring to the following Examples. However, nothing in these examples shall be taken as a limitation upon the overall scope of the invention.

EXAMPLES

The novel examples below are intended to explain the process (Table 1). The essentially water-clear liquids of low viscosity showed no changes even after 3 months in the temperature range relevant for their storage and/or use (5 to 50° C.). It was possible to dilute them with water within wide limits.

In contact with the human skin, the liquids imparted a pleasant feel even after repeated use. Manual cleaning tests on artificially soiled tiles (model soiling comprising 20% motor oil, 20% 20W50, 20% bearing oil SAE90, 10% grease DIN 51 818, Class 2, 10% fine marine sand, 0.5% Benton® 34, 30% black iron oxide and 9.5% coloring black CK2 (Degussa) show a superior cleaning action relative to market products.

|  | 1 | 2 | 3 | 4 | 5 | 6 | 7 | 8 | 9 |
|---|---|---|---|---|---|---|---|---|---|
| Oils |  |  |  |  |  |  |  |  |  |
| Isopropyl myristate | 35 | 33 | 28 | 7.5 | 5 | — | 0.5 | 7.5 | 15 | 25 |
| Liquid paraffin* | — | 2 | — | 0.5 | — | — | — | — | — |
| Miglyol ® 812** | — | — | 5 | — | — | — | — | — | — |
| Pine needle oil*** | — | — | — | 7.5 | — | — | 7.5 | — | — |
| Orange terpene*** | — | — | 2 | — | — | — | — | 1 | — |
| Surfactants |  |  |  |  |  |  |  |  |  |
| $C_{12}$–$C_{14}$-alkylpolyglucoside$_{1,2}$ | 25 | 25 | 25 | 35 | 22.5 | 2.25 | 30 | 35 | 35 |
| $C_8C_{10}$-alkylpolyglucoside$_{1,2}$ | — | — | — | — | 22.5 | 2.25 | — | — | — |

-continued

|  | 1 | 2 | 3 | 4 | 5 | 6 | 7 | 8 | 9 |
|---|---|---|---|---|---|---|---|---|---|
| $C_{12}C_{14}(EO)_7H$ | — | — | — | — | — | — | 5 | — | — |
| $C_{12}C_{14}(EO)_4CH_2COONa$ | — | — | — | — | — | — | — | 3 | — |
| Cosolvents |  |  |  |  |  |  |  |  |  |
| Diethyl tartrate | 15 | 15 | 15 | — | — | — | — | — | — |
| Triethyl citrate | — | — | — | 15 | 4.5 | 0.45 | 15 | 10 | 25 |
| Dipropyl succinate | — | — | — | — | — | — | — | 3 | — |
| Water | ad |  |  |  |  |  |  |  |  |

*DAB [German Pharmacopeia]
**Capryl/capric triglyceride (Hüls)
***Dragoco

This application is based upon German patent Application 196 15 271.2 filed on Apr. 18, 1996, the entire contents of which are herein incorporated by reference.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A cleaning composition comprising a microemulsion, wherein the microemulsion contains:
   (a) an oil;
   (b) water;
   (c) a surfactant containing from 80 to 100% by weight of an alkylpolyglycoside and from 0 to 20% by weight of a compound other than the alkylpolyglycoside; and
   (d) a cosolvent containing an oligoester, wherein the oligoester comprises a carboxylic acid moiety and an alcohol moiety, the carboxylic acid moiety is selected from the group consisting of a polybasic carboxylic acid moiety and a polybasic hydroxycarboxylic acid moiety, and the alcohol moiety contains from 1 to 4 carbon atoms.

2. The composition of claim 1, wherein the alkylpolyglycoside has the formula $$R-O-Z_n$$ 

wherein R is an alkyl moiety containing from 8 to 16 carbon atoms, Z is an oligoglycoside moiety, and n has an average value of from 1 to 3.

3. The composition of claim 1, wherein the alkylpolyglycoside is an alkylpolyglucoside.

4. The composition of claim 1, wherein the alkylpolyglycoside has a mean degree of glycosidation of from 1.1 to 2.

5. The composition of claim 1, wherein the alkylpolyglycoside has a mean degree of glycosidation of from 1.1 to 1.6.

6. The composition of claim 1, wherein the surfactant contains from 0 to 20% of a compound selected from the group consisting of a nonionic compound, an anionic compound, a betaine surface-active compound, and mixtures thereof.

7. The composition of claim 1, wherein the carboxylic acid moiety contains from 2 to 6 carbon atoms.

8. The composition of claim 1, wherein the carboxylic acid moiety contains from 2 to 4 carbon atoms.

9. The composition of claim 1, wherein the alcohol moiety contains from 2 to 4 carbon atoms.

10. The composition of claim 1, wherein the oil contains a compound selected from the group consisting of a monoglyceride, a diglyceride, a triglyceride, a fatty acid ester of a lower alcohol, liquid paraffin, castor oil, and mixtures thereof.

11. The composition of claim 1, wherein the weight ratio of the oil to the water is from 1:1000 to 3:1.

12. The composition of claim 1, wherein the weight ratio of the oil to the water is from 1:500 to 2:1.

13. The composition of claim 1, wherein the weight ratio of the surfactant to the cosolvent is from 1:3 to 100:1.

14. The composition of claim 1, wherein the weight ratio of the surfactant to the cosolvent is from 1:2 to 50:1.

15. The composition of claim 1, wherein the pH of the composition is from 5 to 8.

16. A microemulsion comprising:
   (a) from 0.3 to 50% by weight of oil;
   (b) from 15 to 97% by weight of water;
   (c) from 1 to 60% by weight of a surfactant, wherein the surfactant contains from 80 to 100% by weight of an alkylpolyglycoside and from 0 to 20% by weight of a compound other than the alkylpolyglycoside; and
   (d) from 0.5 to 50% by weight of a cosolvent containing an oligoester, wherein the oligoester comprises a carboxylic acid moiety and an alcohol moiety, the carboxylic acid moiety is selected from the group consisting of a polybasic carboxylic acid moiety and a polybasic hydroxycarboxylic acid moiety, and the alcohol moiety contains from 1 to 4 carbon atoms.

17. The microemulsion of claim 16, wherein the microemulsion comprises from 0.5 to 45% by weight of the oil, from 18 to 95% by weight of water, from 3 to 55% by weight of the surfactant, and from 1 to 45% by weight of the cosolvent.

18. The microemulsion of claim 16, wherein the microemulsion comprises from 1 to 40% by weight of the oil, from 20 to 93% by weight of water, from 5 to 50% by weight of the surfactant, and from 3 to 40% by weight of the cosolvent.

19. The microemulsion of claim 16, wherein the microemulsion has a diameter of from 5 to 100 nm.

20. In a method for cleansing skin or cleaning an inanimate surface, the improvement comprising cleansing the skin or the inanimate surface with a microemulsion formed from a composition, wherein the composition contains:
   (a) an oil;
   (b) water;
   (c) a surfactant containing from 80 to 100% by weight of an alkylpolyglycoside and from 0 to 20% by weight of a compound other than the alkylpolyglycoside; and
   (d) a cosolvent containing an oligoester, wherein the oligoester comprises a carboxylic acid moiety and an alcohol moiety, the carboxylic acid moiety is selected from the group consisting of a polybasic carboxylic acid moiety and a polybasic hydroxycarboxylic acid moiety, and the alcohol moiety contains from 1 to 4 carbon atoms.

* * * * *